US00PP37415P3

(12) United States Plant Patent
Olesen

(10) Patent No.: US PP37,415 P3
(45) Date of Patent: May 12, 2026

(54) MINIATURE ROSE PLANT NAMED 'Poulpah 125'

(50) Latin Name: *Rosa hybrida*
Varietal Denomination: Poulpah125

(71) Applicant: Mogens Nyegaard Olesen, Fredensborg (DK)

(72) Inventor: Mogens Nyegaard Olesen, Fredensborg (DK)

(73) Assignee: POULSER ROSER A/S, Fredensborg (DK)

( * ) Notice: Subject to any disclaimer, the term of this patent is extended or adjusted under 35 U.S.C. 154(b) by 0 days.

(21) Appl. No.: 18/831,799

(22) Filed: Sep. 15, 2025

(65) Prior Publication Data

US 2026/0083032 P1 Mar. 19, 2026

(30) Foreign Application Priority Data

Sep. 19, 2024 (QZ) ..... PBR 20242185

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./101, 116, 122
See application file for complete search history.

(56) References Cited

U.S. PATENT DOCUMENTS

PP24,090 P3 * 12/2013 Olesen ..... A01H 5/02
Plt./122

* cited by examiner

*Primary Examiner* — Susan McCormick Ewoldt

(57) ABSTRACT

A new garden rose plant of the Miniature class which has abundant, red flowers and attractive foliage. This new and distinct variety has shown to be uniform and stable in the resulting generations from asexual propagation.

1 Drawing Sheet

Botanical designation: *Rosa hybrida.*

Variety denomination: 'Poulpah125'.

This application claims priority to Plant Breeder's Rights Application Number 2024/2185, which was filed at the Community Plant Variety Rights Office in the European Union on Sep. 19, 2024, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2016 and the resulting seeds were planted in a controlled environment in Fredensborg, Denmark. The new variety, named 'Poulpah125', originated as a single seedling from the stated cross.

The new variety may be distinguished from its male pollen parent and female seed parent primarily by flower colour. The male pollen parent plant has Red Group 44C flowers while the new variety has Red Group 45A flowers. The female seed parent plant has a flower tonality of Red Group 53A, while the new variety has a flower tonality of Red Group 45A.

The objective of the hybridization of this rose variety was to create a new and distinct variety with unique qualities, such as:

1. Uniform and abundant red flowers with a long shelf-life;
2. Vigorous, but compact growth when propagated on its own roots;
3. Suitability for container production in greenhouses; and
4. Exceptional disease resistance.

This combination of qualities is not present in previously available commercial cultivars of this type, known to the inventor, and distinguish 'Poulpah125' from all other varieties of which we are aware.

As part of the rose development program, Mogens N. Olesen germinated the seeds from the aforementioned hybridization during winter of 2016 and conducted evaluations on the resulting seedlings in a controlled environment in Fredensborg, Denmark. 'Poulpah125' was selected in the spring of 2017 by the inventor as a single plant from the progeny of the aforementioned hybridization.

Asexual reproduction of 'Poulpah125' by rooted cuttings was first done by Mogens N. Olesen in the nursery in Odense, Denmark in July 2017. This initial and other subsequent asexual propagations conducted in controlled environments have demonstrated that the characteristics of 'Poulpah125' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah125'. Specifically illustrated in the drawing are a cluster of flowers on the branch, open flower viewed from above, flower bud, petals detached showing reproductive flower parts, bare stem exhibiting prickles, sepals detached showing the receptacle, mature and juvenile leaves. Plants shown are 3 months old.

DETAILED DESCRIPTION OF THE VARIETY

The following is a description of 'Poulpah125', as observed in its growth in a glasshouse nursery in Odense Denmark. Observed plants are 3 months of age, and were grown on their own roots in 17 cm pots. Color references are made using The Royal Horticultural Society (London, England) Colour Chart, 2001, except where common terms of color are used.

For a comparison, several physical characteristics of the rose variety 'Poulpah053', U.S. Plant Pat. No. 24,090 are compared to the claimed plant. While 'Poulpah125' has about 36 flower petals on average, 'Poulpah053' has about 30 flower petals. The claimed plant has a flower diameter of 50 mm while 'Poulpah053' has a flower diameter of 45 mm. Open flowers of 'Poulpah125' are generally Red Group 45A in color while 'Poulpah053' has a general tonality of Red Group 53B.

FLOWER AND FLOWER BUD

Blooming habit: Continuous.

Flower bud:

- *Size.*—Upon opening, 25 mm in length from base of receptacle to end of bud. Bud diameter is 11 mm.
- *Bud form.*—Ovoid.
- *Bud color.*—As sepals divide petals are Red Group 46B.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—30 mm long, 6 mm wide.
- *Receptacle.*—Texture: Smooth. Size: 6 mm in height, 7 mm wide. Color: Yellow-Green Group 144A. Shape: Long campanulate.
- *Pedicel.*—Surface: Smooth. Length: About 55 mm. Diameter: 2.5 mm on average. Color: Yellow-Green Group 144A. Strength: Strong.
- *Peduncle.*—Length: 10 to 20 mm. Diameter: About 3 mm. Color: Yellow-Green Group 145A. Texture: Smooth.

Flower bud development: Flower buds are borne in clusters of 3 to 4 flower buds per stem.

Flower bloom:

- *Fragrance.*—Moderate.
- *Duration.*—The blooms have a duration on the plant of approximately 25 days. Petals fall cleanly away from plant after flowers have fully matured.
- *Size.*—Flower diameter is about 50 mm when open. Flower depth is 27 mm.
- *Flower shape.*—High centered double, with a high pointed center which is tightly closed.
- *Shape of flower, side view.*—The upper portion is convex. The lower portion is concave.

Petalage: Under normal conditions, flowers have on average, 36 petals.

General Tonality of Flower: Open flowers are Red Group 45A. Color does not change as the flower ages.

Petal color:

- *Upon opening, outer and inner petals.*—Upper surface.—Red Group 46B. Occasionally streaks of Yellow Group 4D. Lower surface: Red Group 53C.
- *Basal petal spots, upon opening.*—Upper surface: Yellow Group 4A, small in size. Lower surface: Yellow Group 4D, small in size.
- *After opening, outer petals.*—Upper surface: Red Group 46B with occasional streaks of Yellow Group 4D. Lower surface: Red Group 53C.
- *Basal petal spots, after opening.*—Upper surface: Yellow Group 4A, small in size. Lower surface: Yellow Group 4D, small in size.

Petals:

- *Petal reflex.*—Strong, bilateral.
- *Margin.*—Entire and uniform. No undulations.
- *Shape.*—Broad and elliptic. Apex shape: Rounded. Base shape: Acute.
- *Size.*—35 mm (l)×38 mm (w).
- *Texture.*—Smooth.
- *Thickness.*—Average.

Petaloids:

- *Size.*—19 mm (l) by 11 mm (w).
- *Quantity.*—About 7.
- *Shape.*—Elliptical with an acute base and rounded apex.
- *Color.*—Red Group 46A on the upper and lower surface. Basal petaloid spots are Yellow Group 4A.

Reproductive flower parts:

- *Pollen.*—None observed.
- *Anthers.*—Size: 2 mm in length. Color: Yellow Group 11B. Quantity: 30 on average.
- *Filaments.*—Color: Green-Yellow Group 1B. Length: 6 mm.
- *Pistils.*—Length: 12 mm. Quantity: 27 on average.
- *Stigmas.*—Color: Yellow-White Group 158A.
- *Styles.*—Color: Red-Purple Group 61C.
- *Location of stigmas.*—Superior in location relative to the length of the filaments and the height of the anthers.
- *Hips.*—None Observed.

PLANT

Plant growth: Upright. Plants are 34 cm in height, and 31 cm wide.

Stems:

- *Color of juvenile growth.*—Yellow-Green Group 144B.
- *Color of mature growth.*—Yellow-Green Group 146A.
- *Length.*—Canes are about 20 cm from the base of the plant to the flowering portion.
- *Diameter.*—Stems are about 4 mm.
- *Internodes.*—On mature canes about 35 mm between nodes.
- *Surface texture.*—Young wood: Smooth. Older wood: Smooth.

Long prickles:

- *Incidence.*—About 9 prickles per 10 cm of stem.
- *Size.*—Average length of prickles on mature stems is 7 mm.

*Shape*.—Upper portion is linear. Lower portion is linear.

*Color*.—Juvenile prickles: Greyed-Purple Group 184C and Greyed-Yellow Group 162D. Mature prickles: Greyed-Purple Group 184C.

Plant foliage:

*Compound leaf*.—About 122 mm (l)×76 (w).

*Quantity*.—3 leaves per 10 cm of stem on average.

*Leaf bearing angle to the stem*.—75 to 90 degrees.

*Color of juvenile foliage*.—Upper side: Yellow-Green Group 144A shaded with Greyed-Red Group 180B. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 6 mm long, 3 mm wide. Quantity: 2 per compound leaf. Shape: Linear, slightly broad based with outward extending apices. Margins: Finely serrated. Color: Yellow-Green Group 144A.

*Petiole*.—Length: About 15 mm. Diameter: 2 mm. Upper surface color: Yellow-Green Group 144A. Lower surface color: Yellow-Green Group 144A.

*Rachis*.—Length: About 56 mm. Upper surface color: Yellow-Green Group 144A. Some intonations of Greyed-Red Group 181A at the point of leaflet attachment. Lower surface color: Yellow-Green Group 144A.

*Leaflet*.—Quantity: Normally 5 to 7 leaflets. Margins: Serrated. Size: Terminal leaflets are about 46 mm long, 29 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of miniature rose plant named 'Poulpah125' substantially as described and illustrated herein.

* * * * *

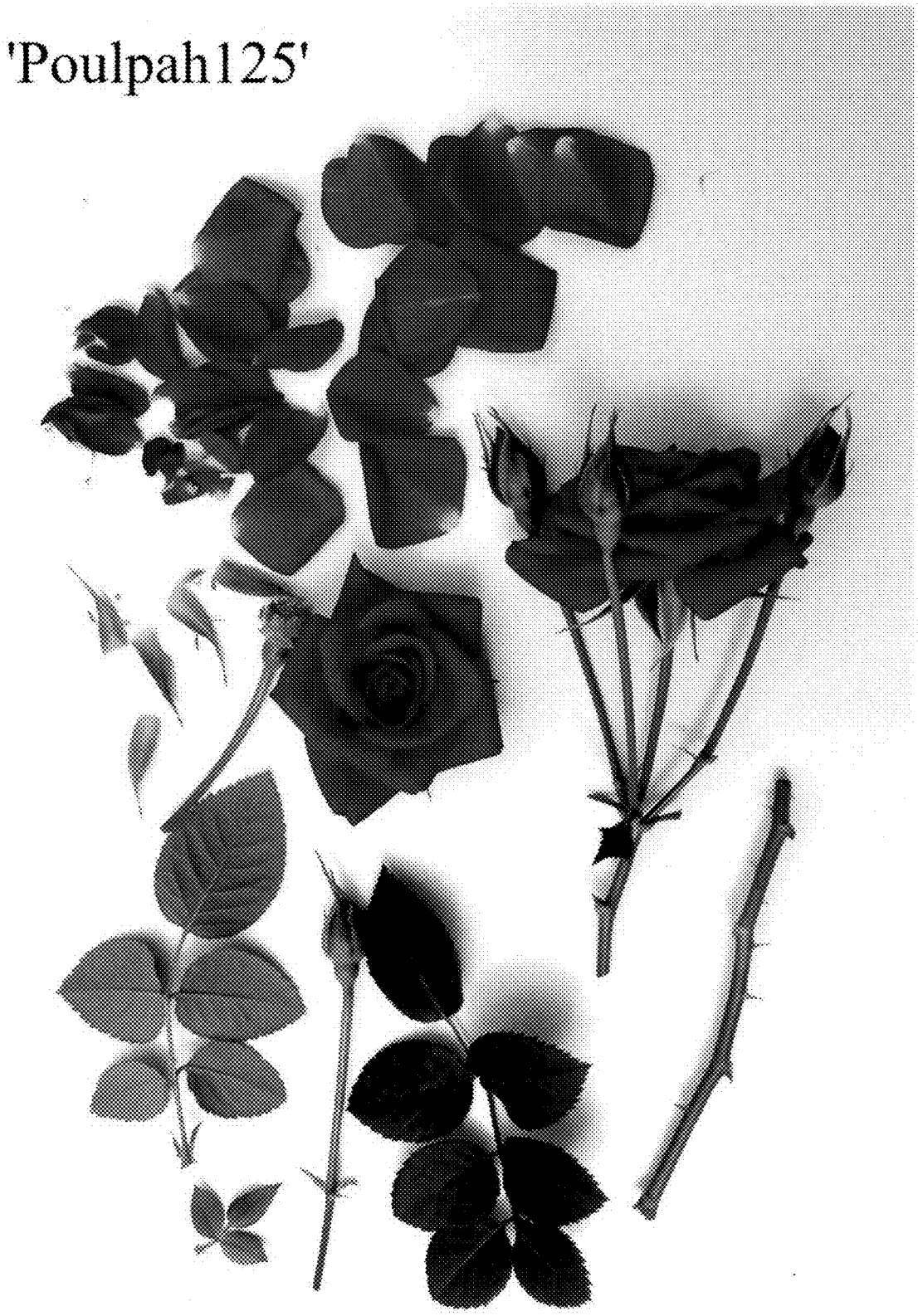
'Poulpah125'